United States Patent [19]

Thornton et al.

[11] Patent Number: 4,595,561

[45] Date of Patent: Jun. 17, 1986

[54] LIQUID SAMPLE HOLDER

[75] Inventors: Michael G. Thornton; Benton C. Clark, III, both of Littleton, Colo.

[73] Assignee: Martin Marietta Corporation, Bethesda, Md.

[21] Appl. No.: 672,464

[22] Filed: Nov. 19, 1984

[51] Int. Cl.[4] .................. G01N 21/03; G02B 21/34
[52] U.S. Cl. ................................ 422/58; 350/536; 356/246; 422/102
[58] Field of Search ............ 422/58, 102, 100; 350/534, 536; 356/246

[56] References Cited

U.S. PATENT DOCUMENTS 3,879,106  4/1975  McCormick ............... 350/536
4,501,496  2/1985  Griffin ........................ 350/536 X

*Primary Examiner*—Arnold Turk
*Attorney, Agent, or Firm*—Yount & Tarolli

[57] ABSTRACT

A liquid sample holder having a fluid sample receptacle bounded by two substantially parallel sheets. The parallel sheets define a fluid analysis area, and adjacent to that area is a peripheral overflow. Air bubbles are trapped in the peripheral overflow because the distance between the plates is smaller than the depth or thickness of the peripheral overflow.

4 Claims, 2 Drawing Figures

U.S. Patent   Jun. 17, 1986   4,595,561
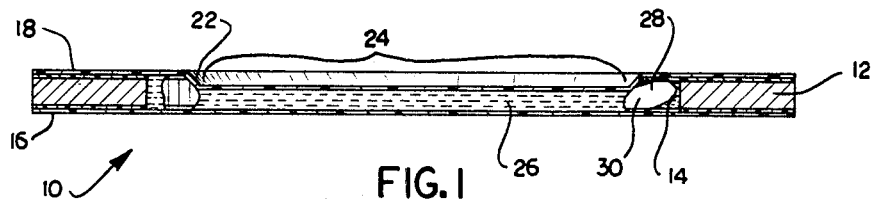
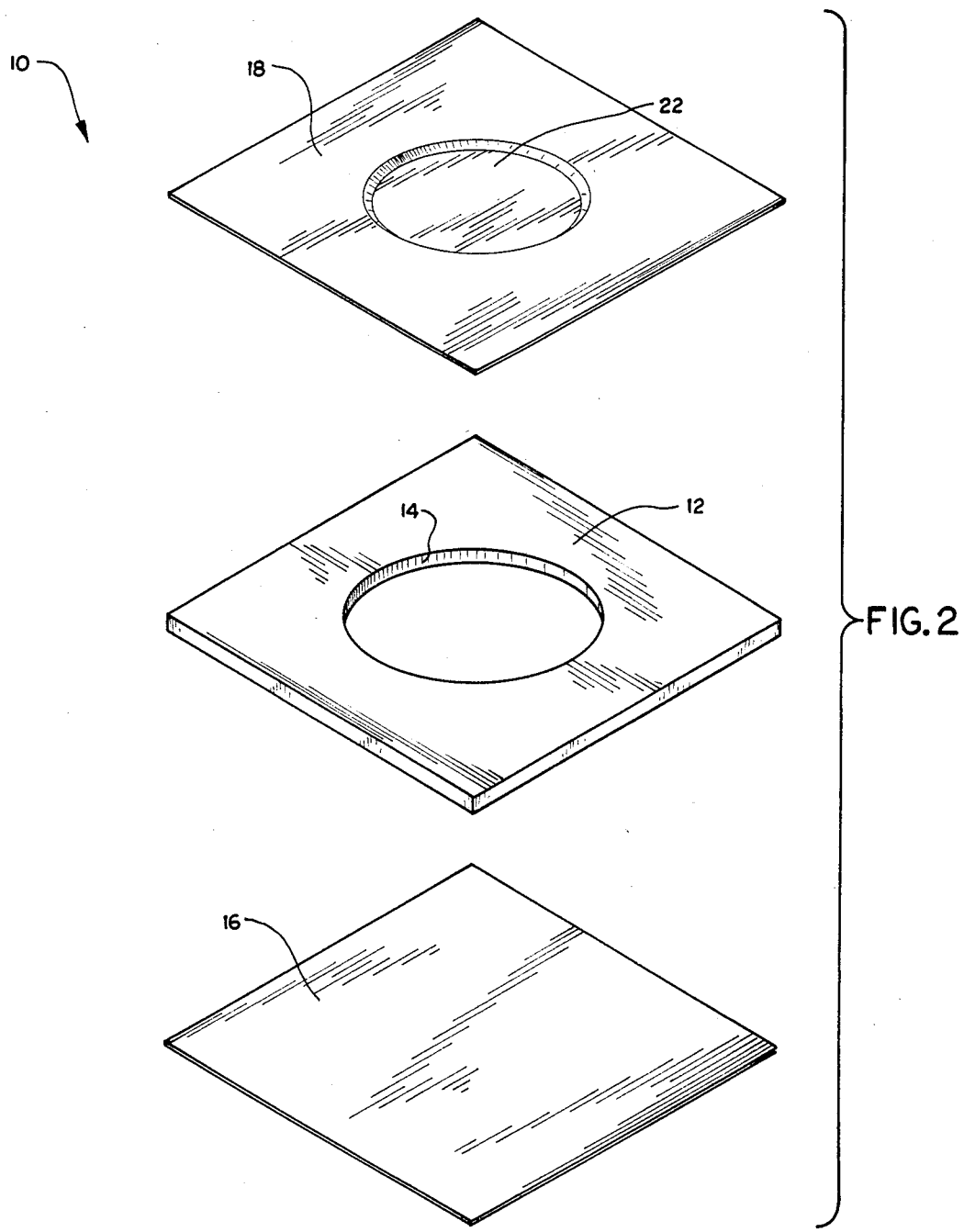

LIQUID SAMPLE HOLDER

FIELD OF INVENTION

The present invention relates to a liquid sample holder.

BACKGROUND OF INVENTION

Prior art liquid sample holders generally require a relatively large quantity of liquid sample for analysis. In X-ray analysis, a liquid sample is generally put into an expendable polypropylene X-ray analysis cell and then covered with a Mylar film which is held in place by a snap ring. When employing X-ray analysis, particularly fluorescence spectroscopy to analyze liquid samples, it has previously been nearly impossible to avoid trapping air bubbles in the analysis area. Also, when air bubbles have been removed from the analysis area, there has been no way to insure that the air bubbles would not migrate back into the analysis area.

SUMMARY OF INVENTION

One object of the present invention is to insure that air bubbles are kept out of the analysis area. Other objects and features include providing a convenient way to store liquid samples for future reference and to provide markings to identify the sample.

The foregoing objects and other advantages and features are achieved by the present invention. The liquid sample holder of the present invention has a sample receptacle bounded on two major surfaces by substantially parallel sheets. The substantially parallel sheets confine the liquid sample to a substantially uniform thickness therebetween, which is important for analysis purposes.

The substantially parallel sheets define a first volume for holding the liquid sample. The first volume is intended to be constant from one sampling analysis to the next to assure a uniform analysis area for the sample. The substantially parallel sheets are composed of a material permitting analysis of the sample to be confined therebetween. The material can vary depending on the analysis technique employed.

A peripheral overflow is provided adjacent the first volume containing the sample in the analysis area. The peripheral overflow is preferably a circumscribing overflow means around the entire periphery of the sample volume to be analyzed. The peripheral overflow has a thickness (i.e., depth) which is greater than the uniform thickness between the two parallel sheets. The greater thickness of the peripheral overflow retains air bubbles in the liquid sample and also receives any excess fluid sample beyond that which is needed to fill the sample volume for analysis.

DESCRIPTION OF DRAWINGS

In the drawings:

FIG. 1 is a cross section of the liquid sample holder of the present invention; and FIG. 2 is an exploded view of the liquid sample holder of the present invention.

DESCRIPTION OF PREFERRED EMBODIMENT

The liquid sample holder of the present invention can take on a variety of shapes as long as the pertinent features as described and claimed herein are employed.

The preferred liquid sample holder 10 is depicted in FIGS. 1 and 2.

The liquid sample holder 10 has a sample frame or spacer 12. The spacer 12 is preferably square, but need not be, and preferably has the dimensions of a 35 mm slide holder. An opening 14 is provided in the spacer 12, and the opening is preferably round for purposes of scientific analysis.

The opening 14 is bounded by a bottom sheet 16 and a top sheet 18. Preferably, the bottom sheet 16 and the top sheet 18 are secured to the two major surfaces of the spacer 12.

In the preferred form, the top cover 18 is provided with a substantially flat depression 22 which is centrally located. The depression 22 of the top cover 18 projects into the opening 14 in the spacer 12. The substantially flat surface 22 of the projection or depression in the cover 18 is substantially parallel to the bottom cover or sheet 16.

The two substantially parallel sheets (16, 22) have a substantially uniform thickness therebetween and define a first volume 26 in the liquid sample holder adapted to hold a liquid sample to be analyzed. It is important for many analysis techniques, particularly X-ray analysis techniques, that the liquid sample be of a uniform thickness and size.

Adjacent the liquid sample volume 26 to be analyzed is a peripheral overflow or reservoir 28. Preferably, the peripheral overflow 28 is adjacent the entire periphery of the liquid sample volume 26. The peripheral overflow 28 has a thickness which is greater than the thickness between the parallel sheets 16 and 22 in the analysis area 24. The lesser thickness in the analysis area 24 for the liquid sample 26 tends to retain air bubbles 30 in the peripheral overflow 28 and also permits excess liquid sample to overflow into the peripheral overflow 28.

The materials for the covers 16, 18 and the spacer 12 can vary widely depending on the analysis technique employed. Suitable materials can be easily selected to be compatible with the sample and the analysis technique. In the preferred form of the present invention, the spacer is a square nylon or aluminum sheet having a circular hole approximately 1¼ inch diameter. The thickness of the spacer 12 varies depending on the volume of sample to be analyzed, but it is generally in the range of 0.040 inches to about 0.080 inches. The bottom sheet 16 is preferably made of Mylar or Kapton (a polyimide from Dupont). Kapton is preferred for X-ray analysis because it has fewer impurities than Mylar. For visual miscroscopic analysis, a thin Mylar film or glass would be suitable. The bottom cover 16 is typically from about 0.00025 inches to about 0.001 inches thick.

The top cover 18 is preferably made of a deformable plastic material such as nylon. Typically, the centrally located depression 22 is about 0.020 inches in depth from the remaining surfaces of the top cover 18.

A suitable bonding technique can be used to adhere the top and bottom covers to the spacer. Solvent resistant adhesives are preferred, and with the materials set forth above, a high temperature acrylic adhesive, such as 3M 966, is preferred. For ease of assembly, it is preferred to apply the adhesive to the spacer 12 and cover the adhesive with a protective backing until assembly of the liquid sample holder is desired.

The top cover 18 can be fabricated by any suitable process such as molding, stamping or the like. Vacuum forming a nylon or other suitable plastic material is preferred because of the ability easily to create different thicknesses for the depressed area 22 in the cover 18. The variations in thickness can be achieved by using different support discs in a standard vacuum forming process. By changing the thickness of the support disc and the die shape, it is possible to adjust the volume available to trap air bubbles when the nylon cover sheet 18 is placed on top of the spacer 12.

Vacuum deforming, or other similar process, is also preferred since suitable markings can be easily placed on the nylon cover sheet to identify sample location or center and other sample identifiers.

If the spacer 12 is previously provided with the film adhesive and backing material, the backing material is first removed. The lower cover 16 is then applied to the spacer 12. Liquid sample is then put into the opening 14 in the spacer 12. Next, the nylon cover sheet 18 is secured to the top surface of the spacer 12.

The depression 22 in the top cover 18 must be great enough to have sample fluid in contact with the top and bottom covers 16, 18 over the entire analysis area 24. This permits any air bubbles to be confined to the peripheral overflow 28, which also accommodates any excess sample flow. Uniform analysis techniques require that a substantially uniform size liquid sample 26 be presented for analysis. Thus, not only should the thickness of the liquid sample 26 be substantially uniform for comparative samples, but also the total volume of the sample to be analyzed should be uniform for comparison purposes.

Separate top and bottom covers 16, 18 and a spacer 12 are used for ease of assembly. If desired, the spacer 12 could be formed as a unitary part with either the top or bottom covers 16, 18. It could also be possible to form all three members as a unitary part so long as the sample could be injected into the liquid sample area 26, such as through the spacer 12 or the peripheral overflow 28.

The projection 22 can be in either the top cover 18 or the bottom cover 16. When the air bubbles have been trapped in the peripheral overflow 28, the liquid sample can be examined with either cover 16, 18 facing "up." In either case, the air bubbles will remain trapped in the peripheral overflow 28. If the sample holder 10 is turned on its edge, the air bubbles will rise to the "top" edge, but still will not cross through the center analysis area. Even if air bubbles are forced into the analysis area 24, they may be forced to the peripheral overflow 28 by slightly squeezing the depressed area 22 of the top cover 18 towards the bottom cover 16. Liquid samples may be conveniently stored in a standard 35 mm slide tray for future reference.

The present invention subjects a constant volume of liquid sample for analysis. The volume of liquid sample subjected to analysis has a uniform thickness which is important for many analysis techniques. Other advantages and features include a sample holder which can be easily stored for future reference and which can be easily provided with markings to identify the sample center, region of interest or identifying marks.

What is claimed is:

1. A holder for a liquid sample to be analyzed, said holder comprising:

a first sheet having a surface on which a liquid sample is placed, a spacer having opposite major surfaces and having one major surface abutting said surface of said first sheet, said spacer having surface portions extending transverse to said surface of said first sheet and defining a hole and for confining the liquid sample to an area of said surface of said first sheet defined by said surface portions, a second sheet abutting the other of said major surfaces of said spacer, said second sheet having a projection which projects into said hole and which defines along with said first sheet and said spacer a space volume for the liquid sample to be analyzed and an overflow volume communicating with said space volume and encircling said space volume, said overflow volume having a dimension measured in a direction perpendicular to said surface of said first sheet greater than the dimension of said space volume measured in the same direction for trapping air bubbles and for receiving liquid in excess of that needed to fill said space volume.

2. A holder as set forth in claim 1 wherein said hole and said projection are circular, and the diameter of said hole is greater than the diameter of said projection.

3. A holder as set forth in claim 1 wherein said first and second sheet are secured to said spacer by applying adhesive to respective surfaces thereon.

4. A holder as set forth in claim 1 wherein said first and second sheets and said projection of said second sheet are flat and parallel to each other.

* * * * *